United States Patent [19]
Banks

[11] Patent Number: 5,638,661
[45] Date of Patent: Jun. 17, 1997

[54] METHOD AND PACKAGING SYSTEM FOR PACKAGING A STERILIZABLE ITEM

[76] Inventor: Percival C. Banks, 405 Golden Gate Ave., Pt. Richmond, Calif. 94801

[21] Appl. No.: 574,644

[22] Filed: Dec. 19, 1995

[51] Int. Cl.$^6$ .................. B65B 5/04; B65B 7/08; B65B 25/20; B65B 55/02
[52] U.S. Cl. .................. 53/469; 206/438; 206/440; 206/494; 383/85; 383/87; 53/425
[58] Field of Search .................. 53/458, 459, 464, 53/466, 469, 425; 206/438, 440, 494; 383/59, 77, 82, 83, 85, 87

[56] References Cited

U.S. PATENT DOCUMENTS

| | | | |
|---|---|---|---|
| 2,709,467 | 5/1955 | Hoeppner | 383/87 |
| 3,015,918 | 1/1962 | Schoen | 383/87 X |
| 3,503,759 | 3/1970 | Wilton | 53/469 |
| 3,960,314 | 6/1976 | Faiers | 383/87 |
| 3,973,567 | 8/1976 | Srinivasan et al. | 383/87 X |
| 3,988,873 | 11/1976 | Oliverius | 53/469 X |
| 4,332,347 | 6/1982 | Clayton | 383/87 |
| 4,677,684 | 6/1987 | Gatward | 383/87 |
| 4,756,628 | 7/1988 | Branson | 383/87 X |
| 5,163,554 | 11/1992 | Lampropoulos et al. | 53/469 X |
| 5,222,600 | 6/1993 | Stoddard et al. | 383/87 X |

*Primary Examiner*—Horace M. Culver
*Attorney, Agent, or Firm*—Chernoff Vilhauer McClung & Stenzel

[57] ABSTRACT

A method and a packaging system for packaging a sterilizable item for aseptic presentation onto a sterile field are disclosed. The packaging system for the sterilizable item includes a sterilizable flexible elongate tubular member having an outside, a closed end and an open end having a circumference. The item is placeable in the tubular member proximate the closed end. The tubular member includes a border portion having a width, an attached edge and an opposing edge spaced apart from the attached edge by the width. The attached edge is attached to the tubular member proximate the open end along the circumference of the open end and the opposing edge is located proximate the outside of the tubular member. The opposing edge receives thereunder the attached edge of the border portion to enclose the item in the tubular member. The packaging system also includes a sterilizable container for receiving therein the tubular member and the item. After sterilization, the item can be dispensed from the sterile tubular member and transferred onto a sterile field by a single non-scrubbed attendant while maintaining the sterility and integrity of the item and the field. The sterile item can be removed from the packaging system in a manner that prevents the inadvertent contamination of the sterilized item. In addition, once the item has been dispensed the elongate tubular member can be used as a convenient waste container during and immediately after the surgery.

10 Claims, 3 Drawing Sheets

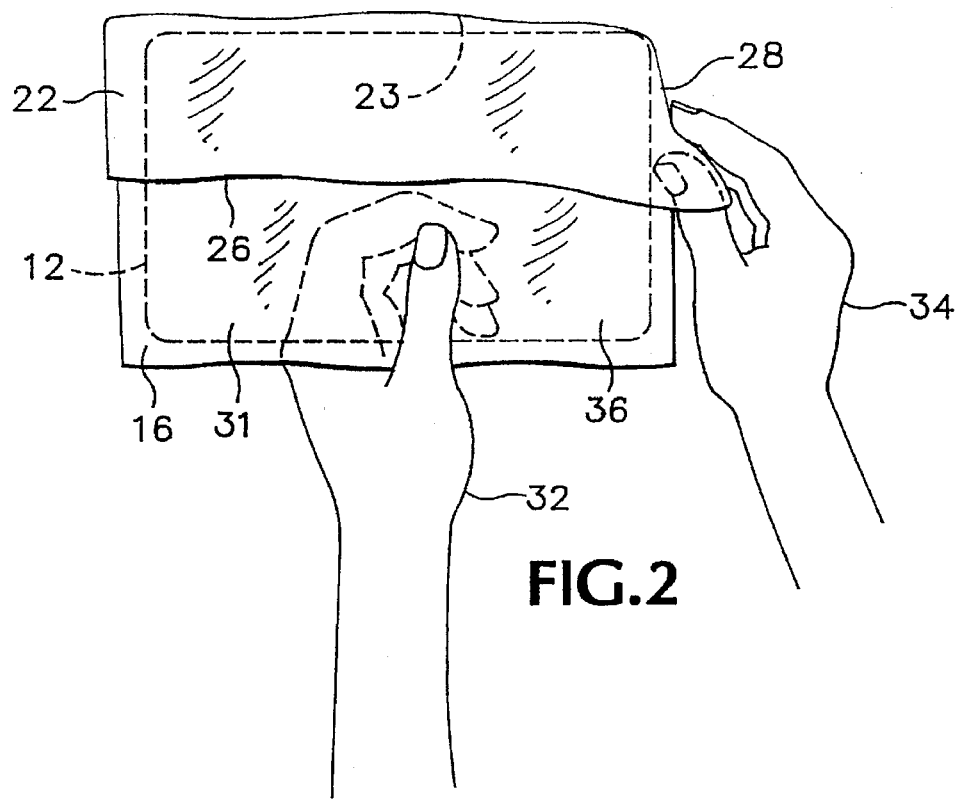
FIG.2
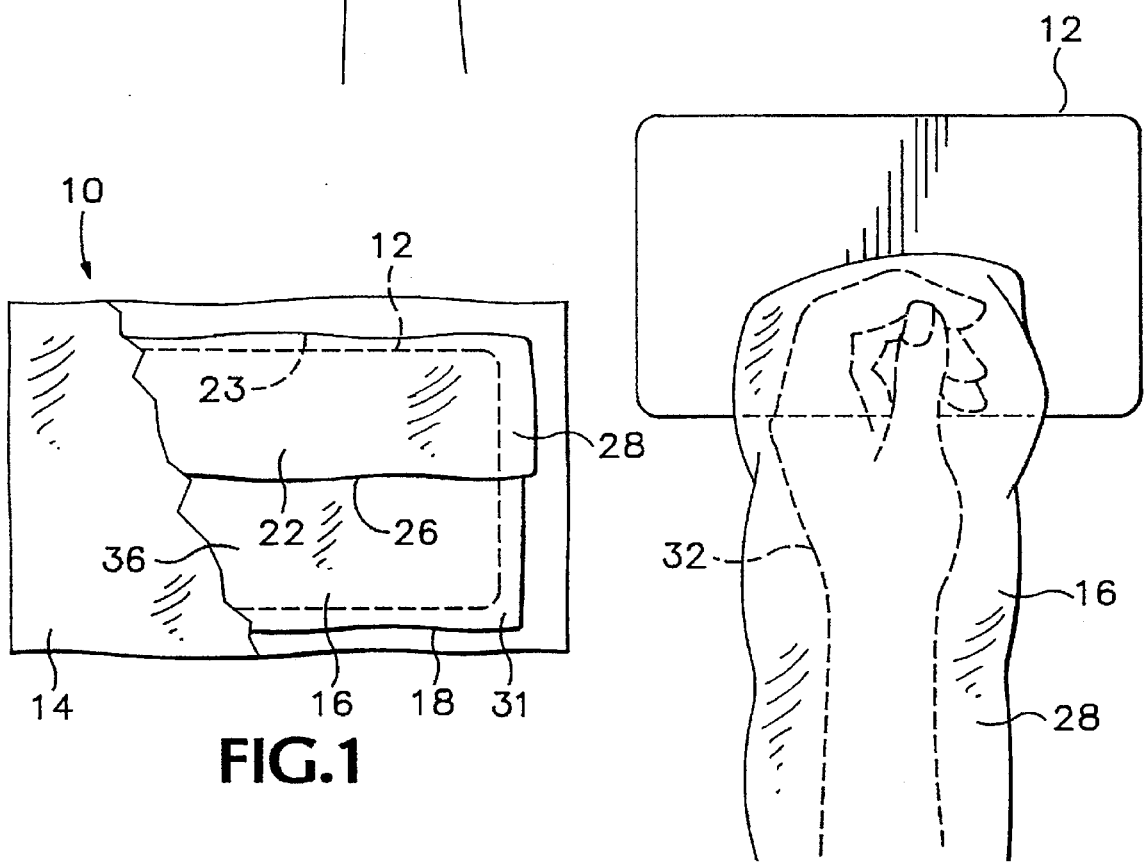
FIG.1
FIG.7

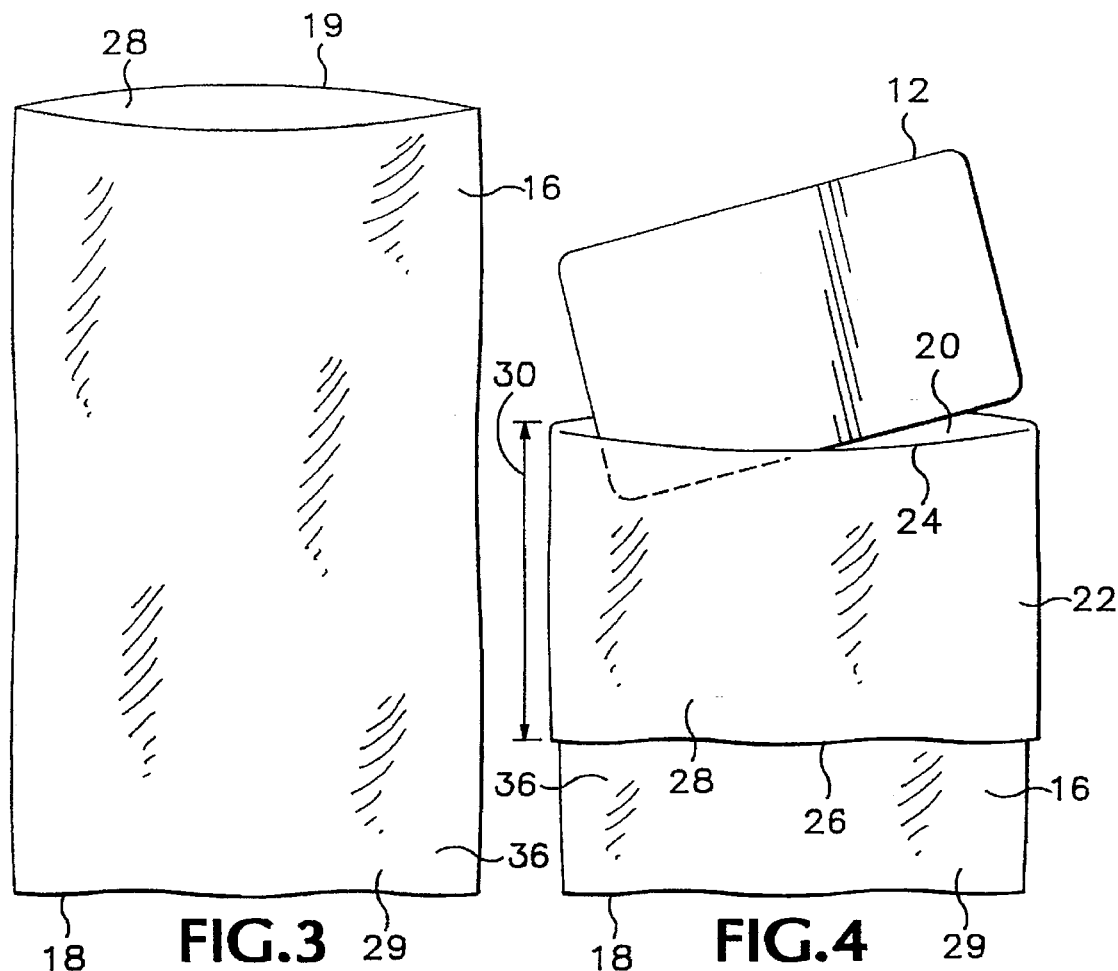
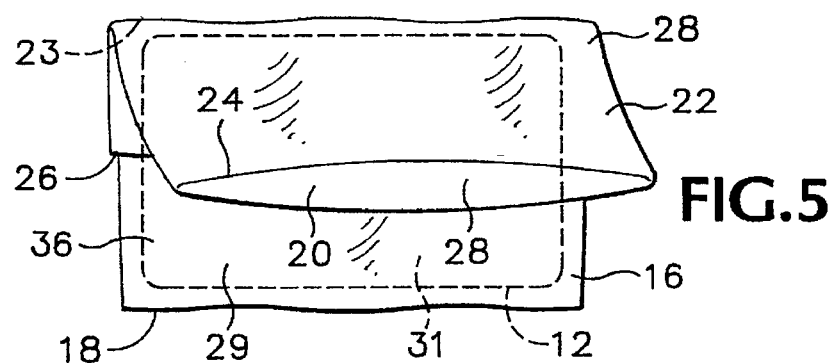
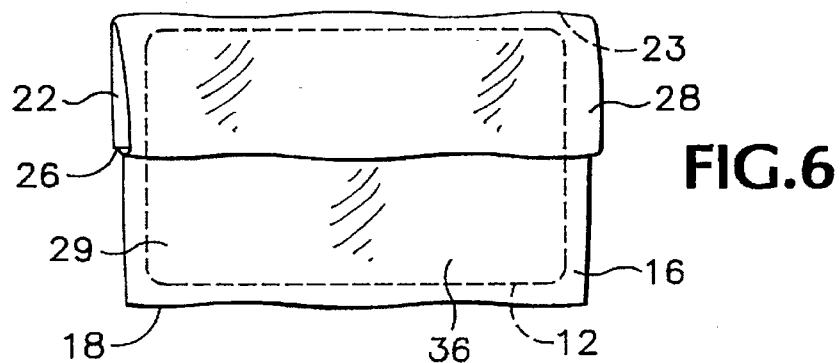

METHOD AND PACKAGING SYSTEM FOR PACKAGING A STERILIZABLE ITEM

BACKGROUND AND SUMMARY OF THE INVENTION

The present invention relates to a packaging system, and more particularly to a packaging system and method for packaging a sterilizable item for aseptic presentation onto a sterile field.

Since the days of Joseph Lister medical professionals have recognized the need for maintaining sterile conditions, especially in an operating room. Thus, under standard operating room procedure sterile equipment covers and patient drapes protect and define a sterile surgical field, and all items within the defined surgical field must be sterile.

Such items as equipment covers, patient drapes, and other medical supplies may be used only a single time, and ready-to-use items are frequently purchased from commercial manufacturers. Alternatively, the items, whether reusable or single-use, may be processed within a facility providing health care such as a hospital, surgical center, clinic or office. The item processor must package the item in a manner that will protect and maintain both the sterility of the item and the sterility of the surgical field during the introduction of the item onto the surgical field. In practice this has meant that many items intended for use in a surgical field are double packaged: a completely sealed outer packaging element surrounds an inner packaging element in or on which the sterilizable item is located. At some point in the production cycle the double-packaged item is sterilized so that when the item arrives at the point of use, both the item and the inner packaging element are sterile.

To introduce a double-packaged sterile item onto a sterile field, typically a non-scrubbed attendant opens and discards the outer packaging element surrounding the inner packaging element and the item. The attendant then carefully opens the inner packaging element and presents the sterile item to scrubbed personnel for transfer to the sterile field. The non-scrubbed attendant must exercise great care in order to maintain the sterility and integrity of the item and thus of the sterile field.

The inner packaging element is intended to provide a second level of protection and to maintain the sterility of the item and of the sterile field during introduction of the item onto the sterile field. An example of a typical inner packaging element is a sheet of material folded in a so-called central supply wrap (CSR), a name that originally identified a hospital central supply department as the source of the packaged item. The name now designates a particular type of an envelope fold.

In a central supply wrap, an item is placed on a diagonal in the center of a square sheet of fabric that is proportionally sized to adequately enclose the item. Each corner of the sheet is folded over the item sequentially, and the fourth corner is tucked under the first three proximate the center of the item, with an end of the fourth corner left exposed for later opening of the package. To facilitate opening a CSR package, the end of each corner may be folded back upon itself to provide a tab for the package opener to grasp.

When opening a CSR package, the non-scrubbed attendant holds the package in a holding hand and with the other hand grasps the exposed corner at the tab, pulls the corner of the sheet away from himself or herself around and under the holding hand, and tucks the corner into the holding hand. The attendant pulls each corner of the sheet away from the item and around the holding hand, tucking the corners between the fingers of the holding hand to provide a protective hand cover. Since only the holding hand has a protective cover when the item has been exposed, the non-scrubbed attendant preferably is assisted by a second, scrubbed, person who removes the sterile item from the holding hand and who actually introduces the sterile item onto the sterile field.

When the non-sterile attendant is opening the CSR package, if any edge of the sheet escapes the holding hand or inadvertently touches the sterile item as it is being exposed, the item has been contaminated. Of course, if the attendant is unaware of the contamination and introduces the item onto the sterile field, the entire field has been contaminated. Such a contamination increases the potential for post-operative infection, currently occurring at a rate of about 7% nationally, which increases both the cost and the risk of the medical procedure. Even discarding the contaminated item increases the cost of the procedure, in terms of actual items used and total time expended during the procedure.

Thus, a need exists for a packaging system for a sterilizable item that permits opening of the system without significant risk of contamination or damage to the item and that permits easy aseptic presentation of the item for use.

According to one aspect of the present invention such a need is satisfied by placing a sterilizable item into a sterilizable tubular member so that the item contacts a portion of an inside surface at a closed end of the tubular member. A border portion is formed on the tubular member; a first edge of the border portion is attached to the tubular member proximate an opening in the tubular member for the circumference of the opening and a second opposing edge of the border portion is spaced apart from the first edge by a width of the border portion. A fold line is formed in the border portion and the tubular member above the item. The item is enclosed in the tubular member by placing the first edge of the border portion under the second edge of the border portion between the border portion and the tubular member. After sterilization the item can be dispensed from the sterile tubular member and transferred onto a sterile field by a single non-scrubbed attendant while maintaining the sterility and integrity of the item and the field.

According to another aspect of the invention, a packaging system for a sterilizable item includes a sterilizable flexible elongate tubular member having an outside, a closed end and an open end having a circumference. The item is placeable in the tubular member proximate the closed end. The tubular member includes a border portion having a width, an attached edge and an opposing edge spaced apart from the attached edge by the width. The attached edge is attached to the tubular member proximate the open end along the circumference of the open end and the opposing edge is located proximate the outside of the tubular member. The opposing edge receives thereunder the attached edge of the border portion to enclose the item in the tubular member. The packaging system also includes a sterilizable container for receiving therein the tubular member and the item. The packaging system can be opened and the item dispensed onto the sterile field in a manner that prevents the inadvertent contamination of the sterilized item. In addition, after the item has been dispensed the elongate tubular member can be used as a convenient waste container during and immediately after the surgery.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is a representation of an exemplary packaging system for a sterilizable item embodying the present invention.

FIG. 2 is a representation of an inner packaging element for the packaging system shown in FIG. 1.

FIGS. 3–6 illustrate the placement of a sterilizable item into the inner packaging element shown in FIG. 2.

FIG. 7 is a representation illustrating the aseptic presentation of the item shown in FIG. 2.

DETAILED DESCRIPTION OF THE PREFERRED EMBODIMENTS

Figures 9, 10:
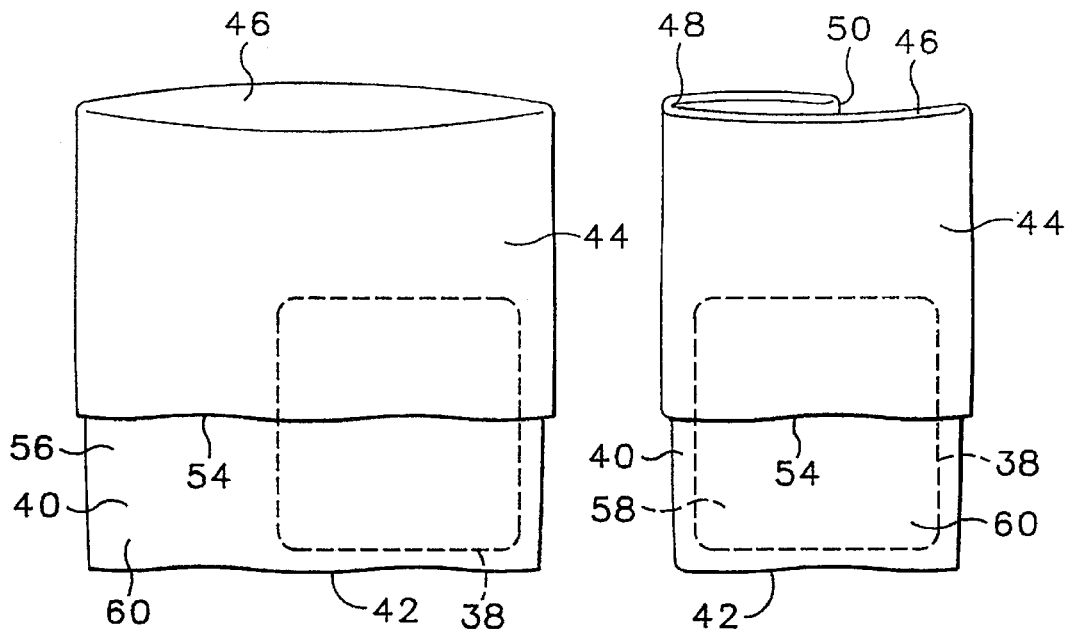
FIGS. 9–12 illustrate the placement of a sterilizable item into the inner packaging element shown in FIG. 8.

Referring now to an exemplary first embodiment illustrated in FIGS. 1–7, a packaging system 10 for a sterilizable item 12 includes an outer packaging element 14 surrounding an inner packaging element. The inner packaging element is a sterilizable flexible tubular member 16 having a closed end 18 and an open end 19 (FIG. 3) and, in a preferred embodiment, resembles a bag made by attaching a bag front to a bag back with at least one side seam and a bottom seam. The tubular member may be made from a reusable fabric such as a woven fabric, or from a disposable single-use material such as a nonwoven fabric or a polymeric film.

The item 12 is placed into the tubular member 16 so that the item contacts a portion of an inside surface 28 at the closed end 18 of the tubular member. The tubular member is sized in proportion to the particular item to be enclosed by the tubular member. In general, the circumference of the open end of the tubular member is preferably about 10–15% larger than the circumference of the item as measured when the item is oriented so that the widest part of the item corresponds with the width of the tubular member.

A border portion 22 is formed on the tubular member 16 so that a first edge 24 of the border portion is attached to the tubular member proximate an opening 20 of the tubular member for the circumference of the opening and a second opposing edge 26 is spaced apart from the first edge 24 by a width 30 of the border portion. The border portion 22 is preferably formed on the tubular member 16 by folding over a circumferential cuff so that a first portion of an outside surface 36 of the tubular member contacts a second portion of the outside surface. A portion of the inside surface 28 of the tubular member is thus exposed and defines the width 30 of the border portion 22 (FIG. 4).

The item 12 is secured in the tubular member 16 to form the inner packaging element. A fold line 23 is formed in the border portion 22 and the tubular member 16 above the item 12, preferably in a manner that permits at least a portion of the inside surface 28 of a first side 29 of the tubular member to be in contact with at least a portion of the inside surface of a second side 31 of the tubular member (FIG. 5), so that the first edge 24 of the border portion is proximate the outside surface 26 of the first side 29 of the tubular member. The first edge 24 of the border portion 22 is then placed under the second edge 26 of the border portion between the border portion and the tubular member (FIG. 6). The width 30 of the border portion 22 preferably is sufficient both to locate the second unattached edge 26 of the border portion proximate the middle third of the item 12 in the tubular member 16, and to permit between a third and a fourth of the width of the border portion to be tucked under the second edge 26. When the first edge 24 of the border portion 22 has been secured under the second edge 26 on the first side 29 of the tubular member, a portion of the second edge remains accessible for grasping on a second side 31 of the tubular member. Tape may be applied to the first side 29, if desired, to tape the border portion 22 to the tubular member 16 to form a tamper-proof seal. The item in the sealed tubular member may also be sterilized without additional packaging.

The packaging system 10 is completed by placing the inner packaging element including the tubular member 16 enclosing the item 12 into the outer packaging element 14. The outer packaging element 14 is a sterilizable container, such as a sealable two-piece, peel-apart pouch, or a CSR cover. The packaging system 10 is sterilized by any convenient method suitable for the item and the materials used in the packaging system. After sterilization, as long as the outer packaging element 14 remains unopened and undamaged the inner packaging element including the tubular member 16 and the item 12 remains sterile and ready to use.

The packaging system 10 is easily opened for aseptic presentation of the sterile item 12. The non-scrubbed attendant opens the outer packaging element 14, for example by peeling apart the two sections of the sealed pouch (FIG. 1), and removing the tubular member 16 of the inner packaging element (FIG. 2). The attendant holds the inner packaging element in one hand 32 at the closed end 18 of the tubular member 16, with its second side 31 and the portion of the edge 26 accessible for grasping facing the attendant. With a second hand 34, the attendant grasps the edge 26 of the border portion 22 at the side of the item 12. The attendant pulls on the edge 26 of the border portion 22, at alternate sides of the item 12, until the first edge 24 of the border portion 22 is released from its tucked-in position between the border portion and the tubular member 16. The attendant continues to pull on the edge 26 until the tubular member 16 has been inverted to expose generally the entire inside surface 28 of the tubular member, while in the process covering the attendant's hand 32 and forearm with the inverted tubular member (FIG. 7). With hand 32 and forearm thus covered and protected, the non-scrubbed attendant may aseptically place the item 12 directly onto the sterile surgical field, eliminating the need for a scrubbed assistant. More importantly, the possibility of inadvertent contamination of the item and the sterile field is eliminated. Thus, one would expect a reduction in the incidence of post-operative infection when using the packaging system of the present invention in the operating room and a concomitant reduction in cost.

Figures 11, 12:
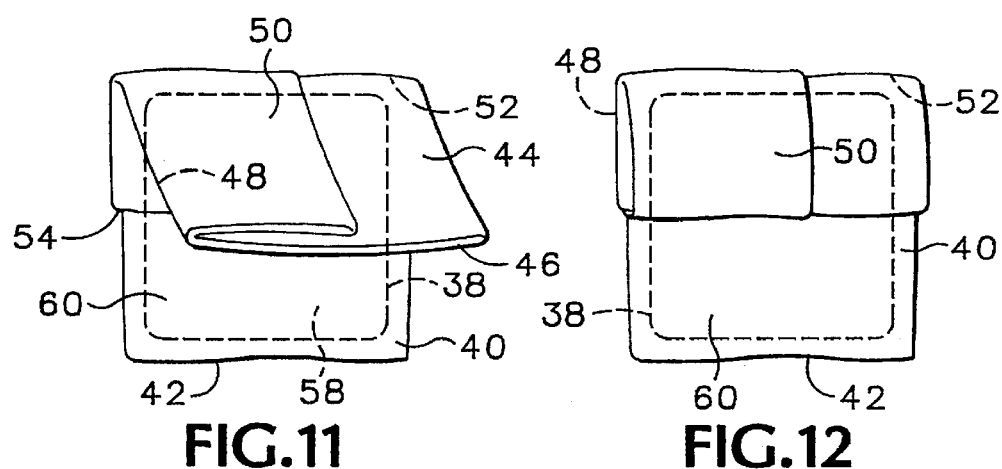
Figure 8:
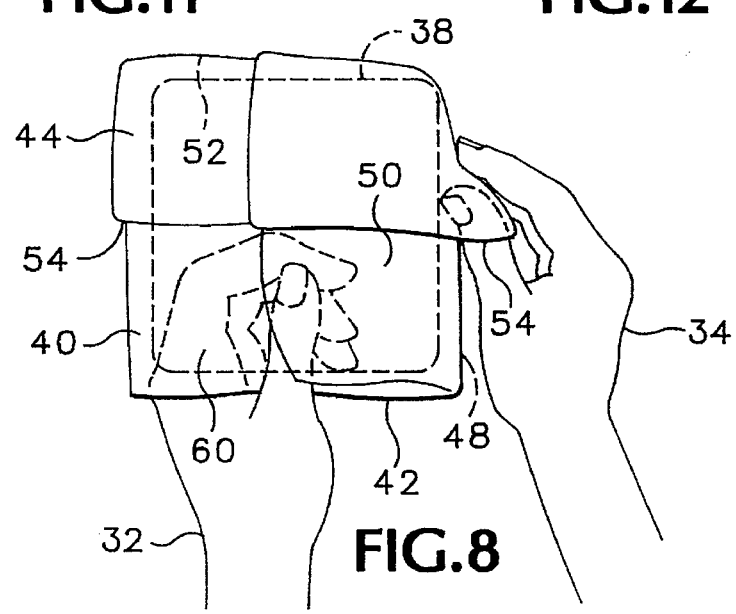
FIG. 8 is a representation of an alternative embodiment of the inner packaging element for the packaging system shown in FIG. 1.

Referring now to an exemplary second embodiment illustrated in FIGS. 8–12, if a sterilizable item is considerably smaller than an available tubular member, an additional step is preferably included in the preparation the inner packaging element of the packaging system. The small item 38 is placed at the closed end 42 of the tubular member 40, and the border portion 44 is preferably formed by folding over a circumferential cuff of the tubular member 40 (FIG. 9) as described above for the tubular member 16, so that a second edge 54 of the border portion 44 is proximate an outside surface 56 of the tubular member at the middle third of the item 38. Before securing a first edge 46 of the border portion 44 under the second edge 54 of the border portion, an additional fold line 48 is formed alongside the item 38 in the border portion and the tubular member. This additional fold line 48 preferably forms a folded-over section 50 so that one portion of the outside surface 56 of the tubular member 40 is in contact with another portion of the outside surface on a first side 58 of the tubular member (FIG. 10). Thereafter, a fold line 52 is formed in the border portion 44 and the tubular member 40 above the item 38, so that the first edge 46 of the border portion is proximate the outside surface 56 of a second side 60 of the tubular member (FIG. 11). The first edge 46 of the border portion 44 is then tucked under the second edge 54 and between the border portion and the tubular member 40 to secure the item 38 in the inner packaging element (FIG. 12).

Alternatively, if the small item itself is, for example, a sheet-like folded item, the excess material of the tubular member which forms the folded-over section 50 described above may instead be tucked into the folds of the item. The fold line 52 is then formed in the border portion 44 and the tubular member 40 above the item 38, and the item 38 is secured in the tubular member 40, as described above, by tucking the first edge 46 of border portion 44 under the second edge 54 between the border portion and the tubular member. As previously described, the inner packaging element preferably is enclosed in an outer packaging element and sterilized.

The small item 38 is removed from the tubular member 40 of the inner packaging element in a manner similar to the manner in which the item 12 is removed from its inner packaging element. The non-scrubbed attendant removes the inner packaging element from the outer packaging element. The attendant holds the inner packaging element in one hand 32 at the closed end 42 of the tubular member 40, with a thumb located under the folded-over section 50 (FIG. 8) and with the second side 60 facing the attendant. With the other hand 34 the attendant grasps the unattached edge 54 of the border portion 44. The attendant pulls on the unattached edge 54 of the border portion 44, at alternate sides of the item 38, until the first edge 46 of the border portion 44 is released from its tucked-in position between the border portion 44 and the tubular member 40, as previously described for removing the item 12 from the tubular member 16. The attendant continues to pull on the edge 54 until the tubular member 40 has been inverted and covers the attendant's hand 32 and forearm. With hand and forearm thus covered and protected, the non-scrubbed attendant may aseptically transfer the item 38 directly onto the sterile field. When the item has been transferred to the sterile field, the tubular member 40 can be used as desired, for example, as a foot switch drape or a waste receptacle for surgical discards such as lap sponges.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method for packaging a sterilizable item for aseptic presentation, comprising:

(a) placing the item into a sterilizable tubular member so that the item contacts a portion of an inside surface at a closed end of said tubular member;

(b) forming a border portion on said tubular member, a first edge of said border portion being attached to said tubular member proximate an opening in said tubular member for the circumference of said opening and a second opposing edge of said border portion being spaced apart from said first edge by a width of said border portion;

(c) forming a fold line in said border portion and said tubular member above said item; and (d) thereafter placing said first edge of said border portion under said second edge of said border portion between said border portion and said tubular member.

2. The method of claim 1 wherein in step (c) at least a portion of said inside surface of a first side of said tubular member is in contact with at least a portion of said inside surface of a second side of said tubular member.

3. The method of claim 1 wherein said border portion is formed by folding over a circumferential cuff so that a first portion of an outside surface of said tubular member is in contact with a second portion of said outside surface of said tubular member, and a portion of an inside surface of said tubular member defines said width of said border portion.

4. The method of claim 3 wherein a second fold line is formed so that a third portion of said outside surface of said tubular member is in contact with a fourth portion of said outside surface of said tubular member.

5. The method of claim 1 wherein said second edge of said border portion is located proximate the middle third of the item in said tubular member.

6. The method of claim 1, including, before step (c), the step of forming a second fold line alongside said item.

7. The method of claim 1, including the step of placing said tubular member into a second packaging element.

8. The method of claim 1, including the step of sterilizing said item.

9. The item packaged by the method of claim 8.

10. The item packaged by the method of claim 1.

* * * * *